US006958043B2

(12) United States Patent
Hissong

(10) Patent No.: US 6,958,043 B2
(45) Date of Patent: Oct. 25, 2005

(54) APPARATUS AND METHOD FOR DISPLACING THE PARTITION BETWEEN THE MIDDLE EAR AND THE INNER EAR USING A MANUALLY POWERED DEVICE

(75) Inventor: James B. Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 172 days.

(21) Appl. No.: 10/151,302

(22) Filed: May 21, 2002

(65) Prior Publication Data

US 2003/0220585 A1 Nov. 27, 2003

(51) Int. Cl.[7] .......................... A61B 5/00; A61M 31/00
(52) U.S. Cl. ..................................................... 600/560
(58) Field of Search ........................... 600/560; 604/36, 604/246, 207, 247; 606/108, 109

(56) References Cited

U.S. PATENT DOCUMENTS

| | | | |
|---|---|---|---|
| 4,757,807 A | | 7/1988 | Densert et al. |
| 5,024,612 A | * | 6/1991 | van den Honert et al. ..... 604/36 |
| 5,421,818 A | | 6/1995 | Arenberg |
| 5,474,529 A | | 12/1995 | Arenberg |
| 5,476,446 A | | 12/1995 | Arenberg |
| 5,746,725 A | * | 5/1998 | Shalon et al. ................ 604/246 |
| 6,159,171 A | | 12/2000 | Densert et al. |
| 6,251,062 B1 | | 6/2001 | Leysieffer |
| 6,629,938 B1 | | 10/2003 | Engvall et al. |

FOREIGN PATENT DOCUMENTS

| | | |
|---|---|---|
| EP | 0 266 474 B1 | 5/1988 |
| WO | WO 00/01346 | 1/2000 |
| WO | WO 00/10484 | 3/2000 |

OTHER PUBLICATIONS

Salt, A. et al "Longitudinal Endolymph Movements and Endocochlear Potential Changes Induced by Stimulation at Infrasonic Frequencies" Acoustical Society of America, pp. 847–856 (1999).

"Transmission of Square Wave Pressure Pulses through the Perilymphatic Fluid in Cats". Acta Otolaryngol (Stockh) 1986; 102: 186–193, Densert, Erlandsson, H. Sheppard.

"Transmission of Low Frequency Pressure Steps to the Perilymphatic Fluid", Acta Otalaryngol 91: 55–64, 1981, Ove Densert, Bjorn Carlborg and John Stagg.

"Immediate Effects of Middle Ear Pressure Changes on the Electrocochleographic Recordings in Parties with Meniere's Disease: A Clinical Placebo–Controlled Study", The American Journal of Otology 18:726–733, 1997, Barbara Densert, Ove Densert Stig Arlinger, Komel Sass, Lars Odkvist.

"Overpressure in Treatment of Meniere's Disease", B. Densert, O. Densert, Halmstad, Sweden, LARYNGOSCOPE, vol. 92, No. 11, Nov. 1982.

"Transmission of Complex Pressure Waves through the Perilymphatic Fluid in Cats", Acta Otalaryngol (Stockh) 1986; 102:403–409, B. Densert, O. Densert, B. Erlandsson and H. Sheppard.

(Continued)

Primary Examiner—Max F. Hindenburg
Assistant Examiner—Brian Szmal

(57) ABSTRACT

Apparatus and method for treating a disease or condition of the ear, such as Meniere's disease or endolymphatic hydrops, includes a manual device operable by hand to pressurize air and pressure transmitting arrangement for delivering the pressurized air to the middle ear, preferably in pulses, to displace the partition between the middle ear and the inner ear to influence fluid in the inner ear.

16 Claims, 6 Drawing Sheets

OTHER PUBLICATIONS

"Functional Patency of the Cochlear Aqueduct", Annals of Otology, Rhinology and Laryngology, Mar.–Apr. 1982, vol. 91, No. 2, B. Densert, B. Carlborg, O. Densert.

"Effects of Middle Ear Changes on Clinical Symptoms in Patients with Meniere's Disease—a Clinical Multicentre Placebo–controlled Study", L.M. Odkvist, S. Arlinger, E. Billermark, B. Densert, S. Lindholm and J. Wallqvist, Acta Otalaryngol 2000; Suppl 543: 99–101.

"Control of Symptoms in Patients with Meniere's Disease Using Middle Ear Pressure Applications: Two Years Follow–up", B. Densert and K. Sass, Acta Otolaryngol 2001; 121: 616–621.

Product Catalog, Medtronic Xomed, Inc., The Meniett ™ Low–Pressure Pulse Generator, Feb. 2003 A Review of Medical Treatment for Meniere's Disease, J. Claes and P.H. Van De Heyning, Acta Otolaryngol 2000, Suppl 544: 34–39.

"Middle Ear Overpressure Treatment of Endolymphatic Hydrops in Guinea Pigs", Yasuhiko Sakikawa and Robert S. Kimura, ORL 1997; 59: 84–90.

\* cited by examiner

APPARATUS AND METHOD FOR DISPLACING THE PARTITION BETWEEN THE MIDDLE EAR AND THE INNER EAR USING A MANUALLY POWERED DEVICE

BACKGROUND OF THE INVENTION

1. Field of the Invention

The invention relates to apparatus and methods for influencing the fluid system of the inner ear for treating the symptoms of Meniere's disease or endolymphatic hydrops and, more particularly, to use of a manually powered device to deliver pressurized air to the middle ear to displace the partition between the middle ear and inner ear of the human ear.

2. Description of the Related Art

Meniere's disease is a chronic disease from which millions of people suffer. The origin of Meniere's disease is believed to be an imbalance in the hydrodynamic system of the inner ear, described as endolymphatic hydrops. In addition to the severity of the symptoms of Meniere's disease, which include fluctuating hearing loss, fluctuating tinnitus, fluctuating sense of fullness in the ear and fluctuating vertigo, the unpredictable onset of the symptoms creates a major handicap for sufferers of Meniere's disease.

As illustrated in FIG. 1, the human ear 10 includes three primary spaces, the outer ear canal 12, also known as the external acoustic meatus, the middle ear 14, and the inner ear 16. The middle ear, also known as the tympanic cavity, is adjacent the outer ear canal and is separated from the outer ear canal by the tympanic membrane 18, also known as the ear drum. The inner ear includes the cochlea 20 formed of the scala vestibuli 22 and the scala tympani 24 which surround the cochlear duct 26 (cross-hatched to simplify visualization). The cochlear duct is filled with endolymphatic fluid supplied by the endolymphatic sac 28. The scala vestibuli 22 and scala tympani 24 are filled with perilymph fluid that moves in response to displacement of the footplate or base 29 of the stapes 30 in the oval window 32. The stapes is one of a series of small bones (ossicles) in the middle ear connecting the tympanic membrane 18 with the inner ear. The inner ear is separated from the middle ear by a partition formed of the stapes footplate at the oval window and the round window membrane 34. Movement of the stapes footplate in the oval window 32 causes the perilymph fluid to move within the scala vestibuli affecting the endolymphatic fluid within the cochlear duct to effect hearing. The round window membrane 34 separates the scala tympani 24 of the inner ear from the middle ear 14 and operates to dissipate waves formed in the perilymph fluid.

The symptoms of Meniere's disease are believed to be caused by endolymphatic hydrops, an excessive buildup of endolymphatic fluid in the cochlea. Meniere's disease is typically characterized by varying degrees of four classic symptoms: 1) fluctuating hearing loss, the extent of which increases over time; 2) fluctuating tinnitus, causing various sounds, described as whining, roaring or other sounds; 3) fluctuating sense of fullness, or a "plugged ear" sensation similar to a sensation one experiences upon descending from a mountain and being unable to clear or equalize the pressure in one's ear; and 4) fluctuating vertigo, or dizziness that can range from mild to severe. As used herein, the terms "symptoms of Meniere's disease" means some or all of the above symptoms in that the method and apparatus of the present invention can provide treatment for any of the above symptoms, individually or together, which are caused by endolymphatic hydrops.

An early method of treating a person with Meniere's disease was developed empirically and includes placing the patient in a pressure chamber to alleviate the symptoms. The theory of the treatment is to place pressure on the inner ear fluids to attempt to reduce the amount of fluid in the endolymph system, specifically the endolymph fluid within the scala media (not shown) of the cochlear duct 26.

Another method includes applying air pressure pulses to the middle ear by way of a hole through the tympanic membrane. The hole allows the pressure pulses to pass from the outer ear canal into the middle ear. It is believed that the round window membrane moves in response to the pressure changes and transfers the movement/pressure changes to the perilymph fluid, which resultantly transfers the motion/pressure changes to the endolymph fluid through membranes separating those two distinct fluids. The oval window may also act to transfer varying pressure to the perilymph fluid; and, accordingly, hereinafter references to displacement of the round window membrane also are meant to include displacement of the stapes footplate at the oval window. U.S. Pat. No. 4,757,807 and U.S. Pat. No. 4,757,807, WO Publications No. 83/02556, No. 93/08775, No. 97/23178, No. 00/01331, No. 00/01346 and No. 00/10484, European Patent No. 266474 B1, Acta Otolaryngol 102:186–193, 1986, Acta Otolaryngol 91:55–64, 1981, Acta Otolaryngol 102:403–409, 1986, Laryngoscope V.92, No. 11, 1982; 1285–92, Carlborg et al 1982 V. 91, No. 2, American Journal of Otology 18:726–733, Acta Otolaryngol 2000 543:99–101 and Acta Otolaryngol 2001 121:616–621 are representative of the above method which is also exemplified by the Meniett portable pressure pulse generator sold by Medtronic Xomed, Inc., Jacksonville, Fla.

In order to practice the above method, a hole formed in the tympanic membrane 18 is fitted with a ventilation tube 36, as shown in FIG. 1. After the ventilation tube 36 is inserted into the tympanic membrane, pressure pulses are generated and transmitted into the outer ear canal 12 by way of a tube having an ear plug sealing the tube against the walls of the outer ear canal so that the pressure pulses vary the pressure in the middle ear through the vent formed by the ventilation tube to influence the fluid system of the inner ear through the round window membrane. That is, the ventilation tube 36 allows air to pass from the outer ear canal 12 to the middle ear 14, thereby allowing the pressure pulses applied to the outer ear canal to cause the pressure in the middle ear to fluctuate. Although the actual mechanisms are still not fully understood, one theory of action that reduces endolymphatic hydrops is that the action of the pressure pulses on the fluid system combine with other physiologic reactions in the ear to force excess endolymph fluid back into the endolymphatic sac 28.

The above method of treating Meniere's disease relies on applying a series of pressure pulses biased by a positive pressure $P_s$, as illustrated in FIG. 2. The pressure pulses are applied to the outer ear canal to transmit varying pressure changes through the ventilation tube 36 into the middle ear in order to displace the round window membrane 34. The series of pressure pulses developed as a result of empirical observations have been used to treat patients suffering from Meniere's disease.

The pressure pulses applied in the past have included sine waves, static and alternating components, a predetermined overpressure superimposed on pressure oscillations, square waves and low frequency sine waves superimposed on square wave pressure pulses. The Densert et al U.S. Pat. No. 6,159,171 shows pressure pulses generated by the Meniett portable pressure pulse generator in FIG. 3 thereof and provides a description thereof in columns 3 and 4.

The above described devices and methods of treating the symptoms of Meniere's disease rely on pressure pulses being generated by complex, electrically powered pneumatic pump arrangements requiring a user to have access to an electrical power source with sufficient capacity to drive the pump arrangement. Accordingly, sufferers of Meniere's disease are limited in when and where they can treat their symptoms of the disease. Further, such pump arrangements have the disadvantages of being bulky, complex and awkward to transport.

SUMMARY OF THE INVENTION

Accordingly, it is a primary object of the present invention to provide manually powered apparatus for generating pressurized air to treat symptoms of a disease of the ear, such as Meniere's disease or endolymphatic hydrops.

Another object of the present invention is to utilize a manual device operable by hand to generate pressurized air for delivery to the middle ear to displace the partition separating the middle ear from the inner ear of a human ear to influence fluid distribution or pressure in the inner ear.

A further object of the present invention is to manually pressurize air and transmit the pressurized air in pulses to the middle ear superimposed on a static pressure greater than ambient air pressure.

Still another objective of the present invention is to increase the portability of apparatus suitable for treating diseases and conditions of the ear, such as Meniere's disease or endolymphatic hydrops.

The aforesaid objects are achieved individually and in combination, and it is not intended that the invention be construed as requiring two or more of the objects to be combined unless expressly required by the claims attached hereto.

In accordance with the present invention, apparatus for treating symptoms of a disease of the human ear, such as Meniere's disease or endolymphatic hydrops, includes a manual device operable by hand to pressurize air and a pressure transmitting arrangement communicating with the manual device to deliver pressurized air to the middle ear to displace the partition between the middle ear and the inner ear to influence fluid in the inner ear. The pressure transmitting arrangement can include a pressure regulator configured to deliver air pressure pulses to the middle ear.

The apparatus and method of the present invention can be used to treat symptoms of Meniere's disease or other ear ailments such as tinnitus, vertigo, hearing loss and fullness of the ear, often associated with Meniere's disease and endolymphatic hydrops.

The above and still further objects, features and advantages of the invention will become apparent upon consideration of the following descriptions and descriptive figures of specific embodiments thereof. While these descriptions go into specific details of the invention, it should be understood that variations may and do exist and would be apparent to those skilled in the art based on the descriptions herein.

DETAILED DESCRIPTION

Figure 1:
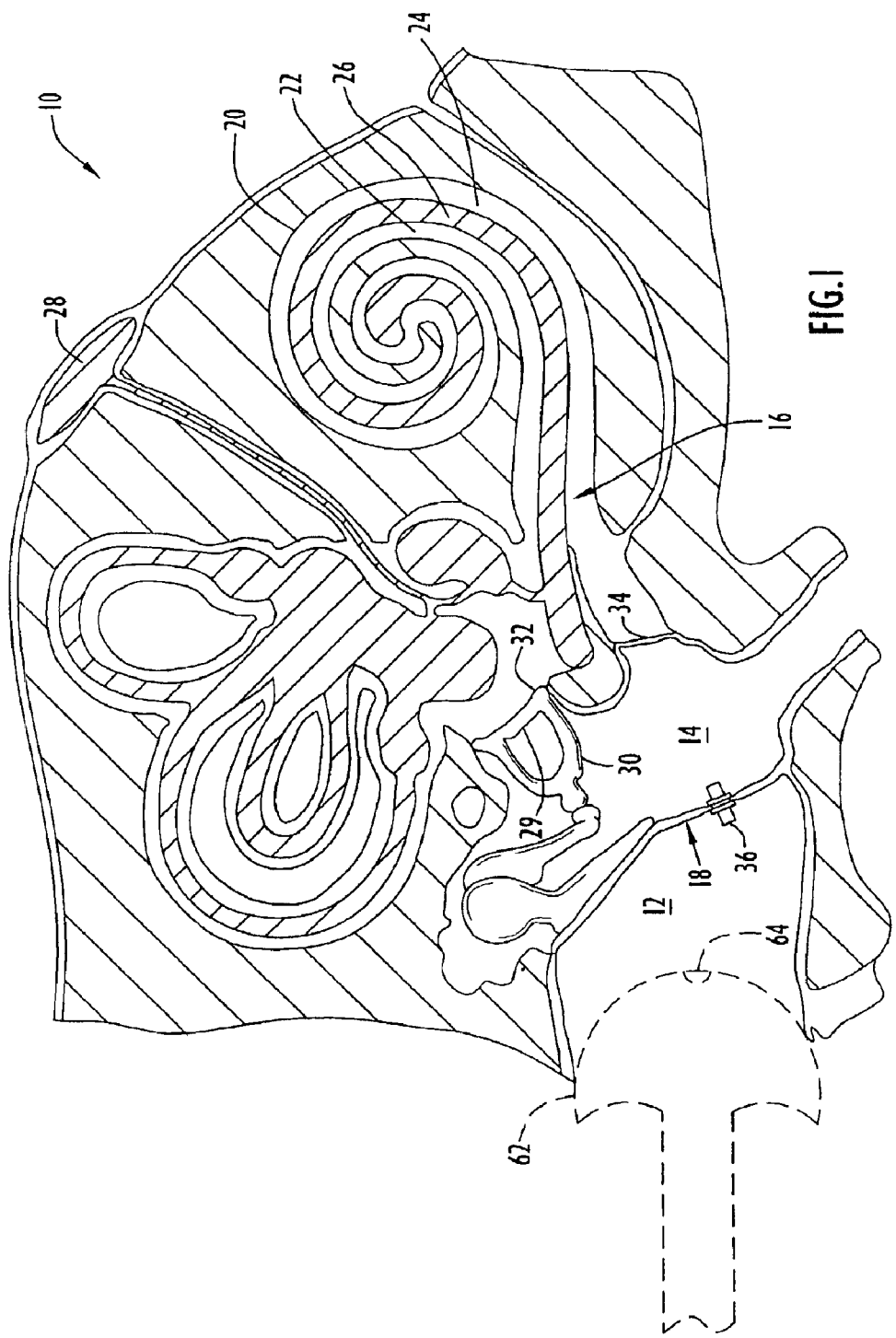
FIG. 1 is a broken section of a human ear showing a portion of the outer ear canal, middle ear and inner ear.

The embodiments described below are described with reference to the above drawings, in which like reference numerals designate like components.

Figure 3:
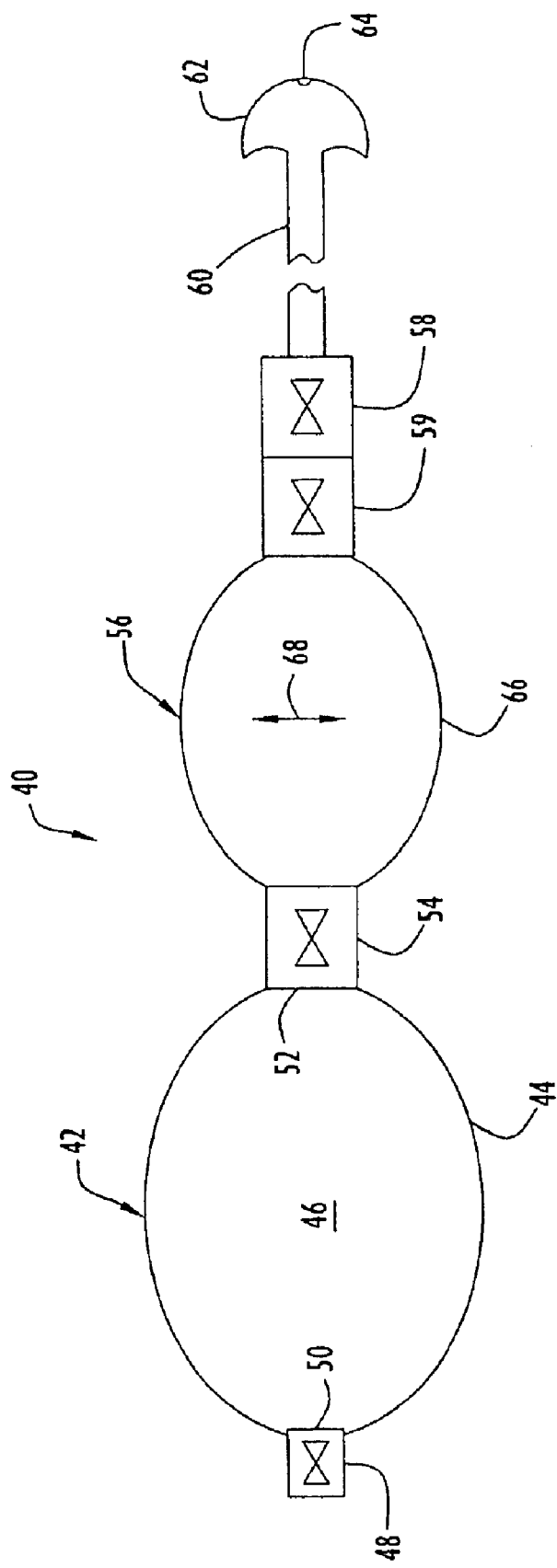
FIG. 3 is a diagram of apparatus according to the present invention.

Apparatus 40 according to the present invention is shown in FIG. 3 and includes a manual device 42, shown as a hollow squeeze bulb, operable by hand to pressurize air. While a squeeze bulb having resilient walls 44 defining a chamber 46 is shown, any manual, hand-operated device could be used to pressurize air in accordance with the present invention, for example a cylinder with a hand-cranked piston movable therein with appropriate valving. A check or one-way valve 48 is disposed in an inlet port 50 at one end of the squeeze bulb allowing air to enter the chamber from the surrounding environment but preventing air from exiting the chamber. Disposed in an outlet port 52 at the other end of the chamber 46 is a check or one-way valve 54 allowing air to exit the chamber but preventing air from entering the chamber therethrough. The check valve 54 controls communication between the chamber 46 and a reservoir 56 receiving pressurized air from the chamber 46 and holding the air under pressure. A pressure regulator 58 communicates with the reservoir 56 via one-way check valve 59 and with a delivery tube 60 which terminates at an ear plug 62, having an aperture 64. The ear plug 62 is shaped to form a seal with the walls of the outer ear canal 12 as shown in dashed lines in FIG. 1.

Figure 2:
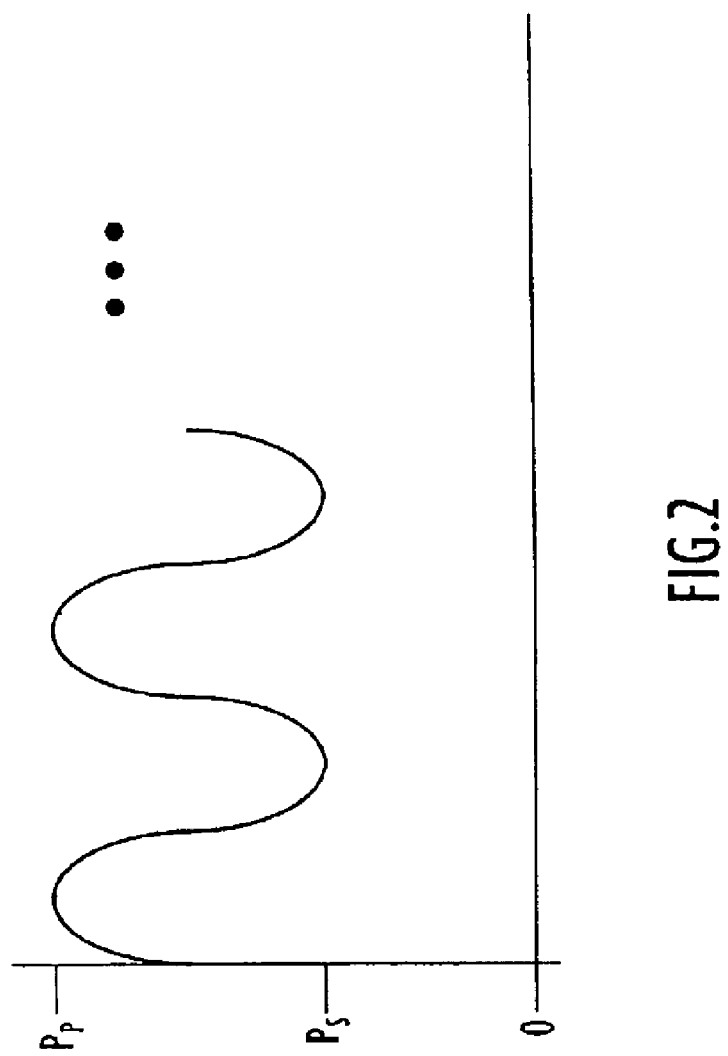
FIG. 2 is a graph of a pressure wave in the form of a sine wave biased by a positive pressure in accordance with the prior art.

The squeeze bulb can have a generally spheroidal hollow configuration with inlet port 50 and outlet port 52 in fluid communication with the chamber formed by the hollow interior. The squeeze bulb is constructed of a resilient and flexible material (e.g., rubber) to facilitate deformation of the bulb in order to expel pressurized air through check valve 54 when the bulb is squeezed, or compressed, and draw air from the ambient environment into the bulb through check valve 48 when the bulb relaxes from the compressed position to a relaxed, expanded position. The squeeze bulb produces a pressure waveform at outlet port 52 illustrated in FIG. 4. When the squeeze bulb is in the relaxed position, the pressure, or air flow rate, at outlet port 52 is zero, as shown by point A in FIG. 4. Upon compressing the squeeze bulb, the pressure, or air flow rate, at the outlet port 52 increases to a pressure $P_{bulb}$, at point B. The pressure then decays, illustrated by the area designated C in FIG. 2, until the bulb returns to its relaxed position at which the pressure is zero or ambient pressure, as shown at point D.

Reservoir 56 can also be generally spheroidal in shape with a hollow interior and includes an inlet port at one end communicating with check valve 54 and an outlet port communicating with check valve 59 at an opposing end. The amount of air pressure held in the reservoir depends on the air pressure generated by the squeeze bulb. The reservoir 56 is defined by resilient, elastic walls 66 having a contracted, relaxed state with air in the reservoir being at or near ambient pressure and having an expanded, under tension, state when air in the reservoir is under pressure greater than ambient pressure such that the walls 66 expand and contract as indicated by the arrow 68. The delivery tube 60 is generally cylindrical in shape and forms a passage extending from the pressure regulator 58 to the aperture or exit port 64 in the ear plug 62.

The pressure regulator 58 includes a simple open/close valve disposed downstream of check valve 59 and can also include a filter or valve configured to regulate air pressure delivered to the exit port 64 of ear plug 62. The delivery tube 60 delivers the pressure waveform into the outer ear canal; and, the ear plug, by sealing against the outer ear canal walls, contains the air pressure within the outer ear canal. The ventilation tube 36 allows the pressure waveform to change the pressure in the middle ear 14 in a similar manner and to displace or move the partition between the middle ear and inner ear.

Figure 4:
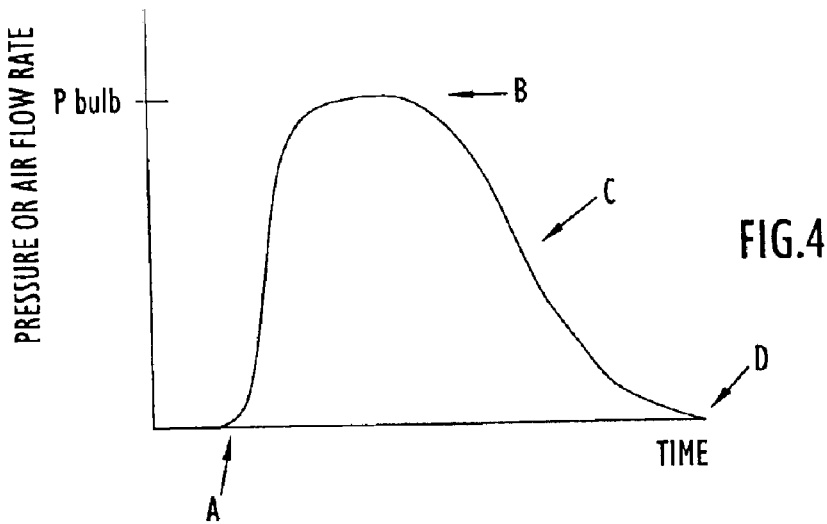
FIG. 4 is a graph of a pressure profile developed by the manual device of the apparatus of the present invention.
Figure 9:
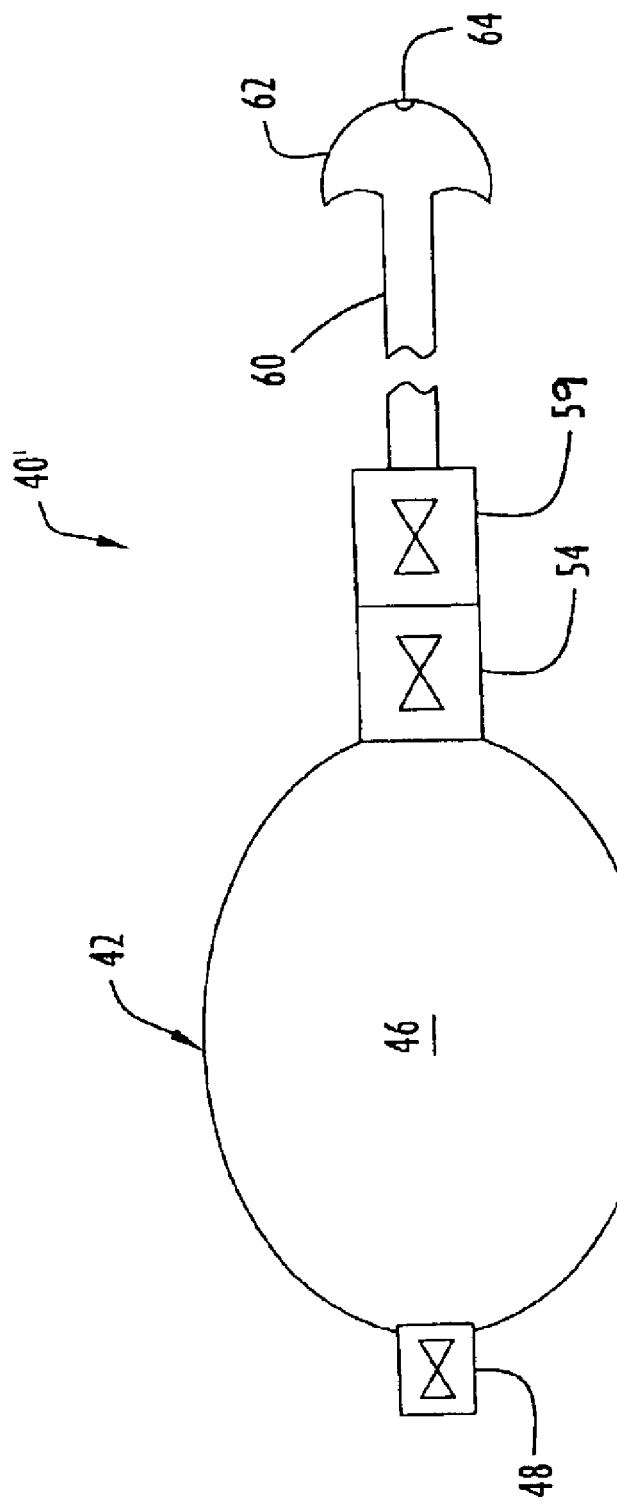
FIG. 9 is a diagram of another embodiment of apparatus according to the present invention.

Design and operation of the pressure regulator 58 permits various pressure waveforms to be delivered to the middle ear along with waveforms formed of square or modified square pulses as would be formed where the pressure regulator is a single, one-way or check valve, as shown in FIG. 4. The waveform shown in FIG. 4 is delivered to the middle ear by squeezing manual device 42 to pressurize air in chamber 46 and force the air into reservoir 56 through check valve 54. The delivered pressure increases after the manual device is squeezed, as shown at A, and increases to a maximum pressure or air flow rate, as shown at B, dependent upon the air pressure generated by the manual device 42, the valve structure in flow regulator 58 and other air flow parameters, such as restrictions. From the maximum pressure B, the pressure or air flow declines, as shown at C, dependent upon the volume of air displaced, compliance of the resilient walls of the reservoir, valve structure in flow regulator 58 and other air flow parameters, such as restrictions, until the pressure returns to ambient, as shown at D. The pulse waveform of FIG. 4 is obtained by using a single open/close valve in the flow regulator downstream of the reservoir outlet check valve. The pressure wave form of FIG. 4 can also be generated by coupling check valve 54 directly with delivery tube 60; however, the use of reservoir 56 permits storage of pressurized air such that a user need not squeeze the manual air pressurizing device while the apparatus is held in place in the outer ear canal. That is, if the apparatus of the present invention takes the form shown in FIG. 9, where the reservoir is not used, the pressure pulse shown in FIG. 4 can be generated; however, the apparatus must be operated to pressurize air with the ear plug sealed in the outer ear canal. If the apparatus includes the reservoir, as is preferred, the reservoir can be filled with pressurized air with the open/close valve in the flow regulator closed prior to sealing the ear plug in the outer ear canal.

The check valve 59 permits flow in one direction from the reservoir into the delivery tube while preventing back flow of air from the delivery tube channel to the reservoir thereby assuring that no negative pressure is applied to the middle ear. The open/close valve in the pressure regulator can be operated by hand to deliver pressurized air pulses similar to FIG. 4 to the middle ear.

Figure 6:
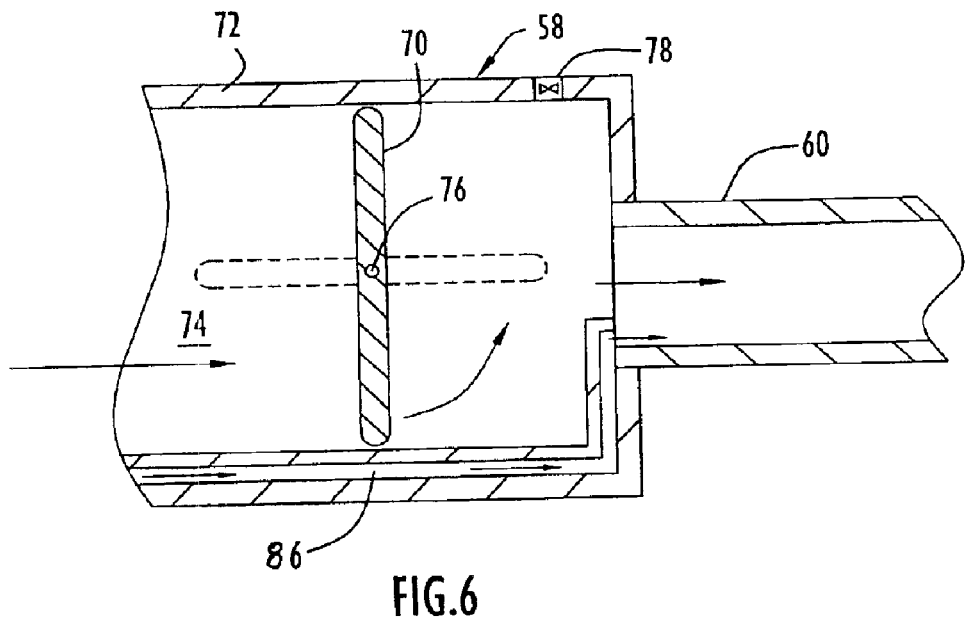
FIG. 6 is a broken section of a pressure regulator for use with the apparatus of the present invention.

An exemplary embodiment of the pressure regulator 58 is illustrated in FIG. 6 and includes a disc-shaped valve member 70 pivotally mounted in a housing 72 to be movable between open and closed positions to control air flow rate and air pressure supplied by delivery tube 60. The housing 72 is cylindrical and defines a main passage 74, and the valve member 70 has a circumferential edge sized to seat or seal against the inner surface of the main passage when the valve formed thereby is in a closed position. The valve member 70 is centrally mounted, similar to a butterfly valve, on a pivot pin or shaft 76 to be rotatable between the closed position, where the valve member is oriented substantially perpendicular with respect to the longitudinal axis of the housing to seat or seal against housing 72 and a fully open position (shown by dashed lines) where the valve member is oriented substantially parallel with respect to the longitudinal axis of the housing. The valve member can have any desired configuration, for example, pivoted off-center similar to a flapper, slide mounted to move transverse to the axis of the housing or having a diameter greater than the diameter of the housing to prevent 360° rotation. The valve member can be moved to various positions between the closed and fully open positions to control or regulate the pressure delivered to the middle ear.

Figure 5:
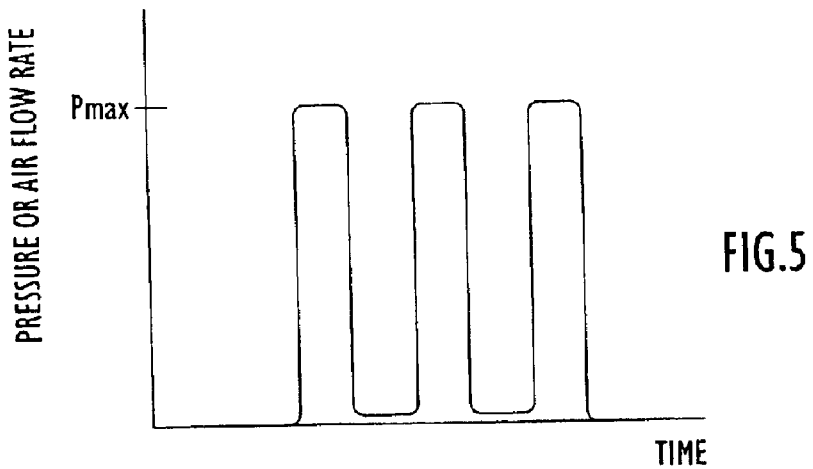
FIG. 5 is a graph of a pressure profile developed at the outlet of the apparatus of the present invention with no static pressure greater than ambient air pressure established.

The pressure regulator 58 as described thus far can operate to generate a pressure waveform as shown in FIG. 5 by the valve member cycling between open and closed positions such that the air pressure delivered to the middle ear will rise and fall in a controlled or cyclical manner. To this end, the valve member can be caused to rotate or oscillate by cyclic response to pressure due to the configuration of the valve member and valve seat and/or mounting of the valve member, for example, an off-center pivoting axis, by mechanical means that can be hand operated or electronically controlled or by electro-mechanical means. When the valve member is open, the air pressure delivered to the middle ear will be $P_{max}$; and, when the valve member is closed, a vent valve 78 downstream of the valve member opens to permit the delivered air pressure to drop to ambient air pressure. By controlling the movement of the valve member, the duration of the pressure pulses can be controlled. Another manner in which the pressure waveform of FIG. 5 can be generated with the use of valve member 70 is to control or cycle the opening and closing of the vent valve 78. This can be accomplished mechanically, electro-mechanically or manually. In the simplest manner, the vent valve can be formed as an opening in the housing with the user using his finger as a valve member.

Figure 7:
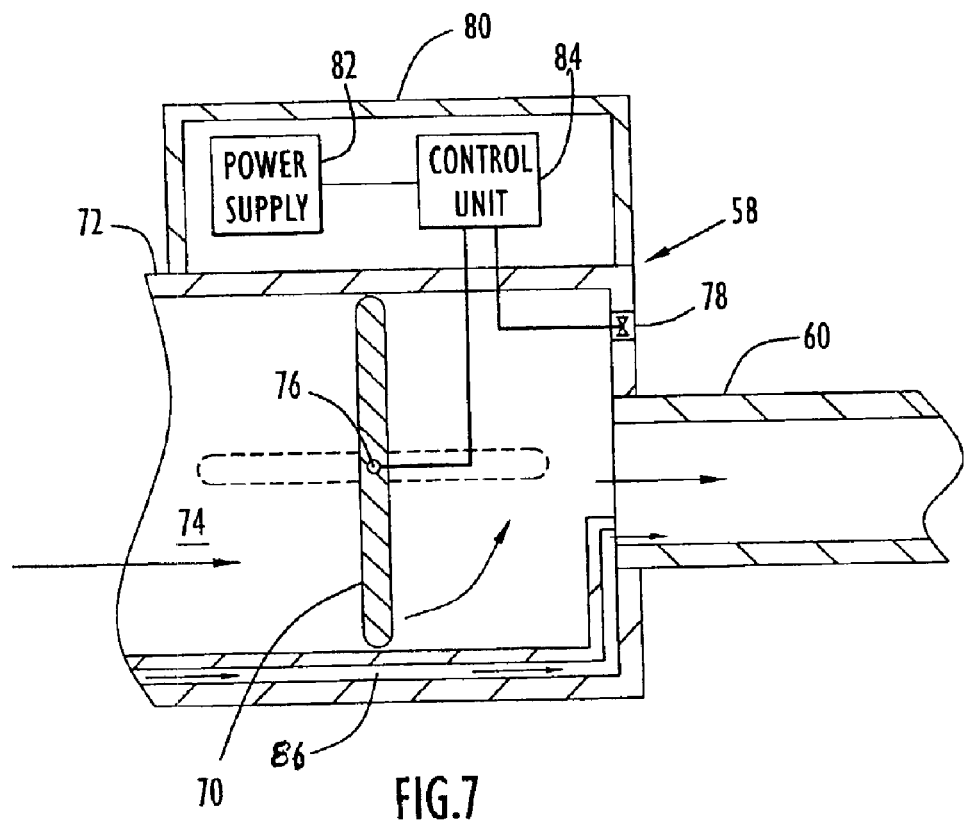
FIG. 7 is a broken section of another embodiment of a pressure regulator for use with the apparatus of the present invention.

Another embodiment of a pressure regulator 58 is illustrated in FIG. 7 and includes a valve arrangement substantially similar to the valve arrangement of FIG. 6 with the addition of an electrically controlled actuator to control movement of the valve member. More particularly, a compartment 80 is carried on housing 72 and houses a power supply 82 (e.g., a battery) and a control unit 84. The power supply provides power to the control unit 84 which includes electronics and motors to control rotation or oscillation of the valve member 70 via shaft 76 and also to control vent valve 78. In order to produce the pressure waveform of FIG. 8, the pressure regulator 58 includes a restricted air flow passage 86 segregated from the main passage 74 and communicating with reservoir 56 via check valve 59 and with delivery tube 60 to provide a continuous supply of air at a static pressure $P_S$ from the reservoir, and the vent valve is either eliminated or remains closed during operation. Accordingly, the varying pressure pulses are superimposed on the static pressure $P_S$ established by air flow passage 86.

The present invention essentially utilizes a manual device operable by hand to pressurize air, which can be formed by manual device 42, and a pressure transmitting arrangement or structure communicating with the manual device and configured to communicate with the outer ear canal to deliver air pressure to the middle ear via a vent in the tympanic membrane, which can be formed by the delivery tube 60 and ear plug 62 alone or in combination with the pressure regulator 58 and/or the reservoir 56. While the manual device 42 is shown as a squeeze bulb, any suitable hand-operated arrangement can be used to pressurize air, for example, a piston movable within a cylinder or a bellows. In use, when no reservoir is included in the apparatus, the ear plug is sealed in the outer ear canal, and the manual device is operated by hand to deliver a pressure pulse via the delivery tube to the middle ear. If a series of air pressure pulses is desired, as is preferred, the manual device can be operated again after a desired period of time to generate further pulses, with appropriate vent valves, if needed, to allow the pressure transmitting arrangement to return to ambient air pressure quickly. Alternatively, the manual device can be operated to provide air pressure sufficient to produce a series of pulses, and the pressure regulator 58 can be included in the pressure transmitting arrangement to generate the series of air pressure pulses.

Figure 8:
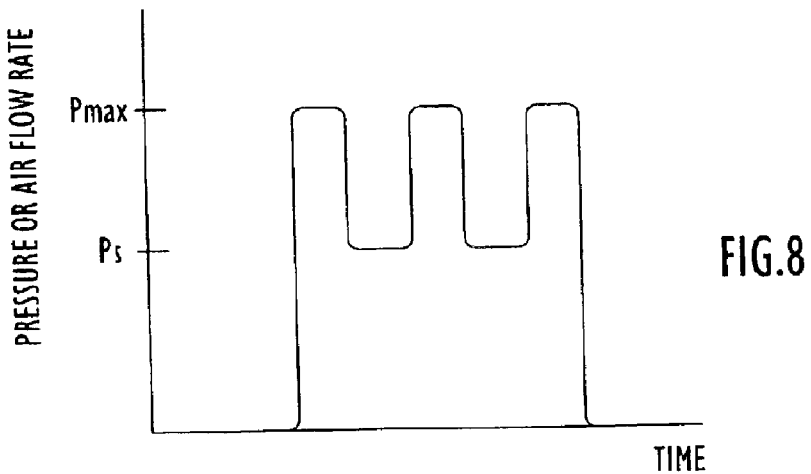
FIG. 8 is a graph of a pressure profile developed at the outlet of the apparatus of the present invention with a positive static pressure greater than ambient pressure.

When the reservoir 56 is included in the pressure transmitting arrangement, the manual device 42 is operated as many times as required to fill the reservoir to the extent, and pressure desired, which expands the walls 66 of the reservoir such that the reservoir maintains the pressure as the walls contract with the release of pressure. The ear plug is inserted in the outer ear canal, and a series of pulses in a pressure waveform, such as the pressure waveforms shown in FIGS. 5 and 8, are applied to the middle ear to displace the partition between the middle ear and the inner ear and influence fluid or stimulate fluid distribution in the inner ear. Additionally, a diaphragm pump can be located between the pressure regulator and the delivery tube to provide pressure pulses responsive to the pulses from the pressure regulator.

Having described embodiments of manually powered apparatus and methods for treating the human ear to displace the partition between the middle ear and the inner ear, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in their ordinary and accustomed manner only, unless expressly defined differently herein, and not for purposes of limitation.

What is claimed is:

1. Apparatus for treating a human ear having an outer ear canal separated from a middle ear by a tympanic membrane with a vent therethrough and an inner ear separated from the middle ear by a partition to treat the symptoms of Meniere's disease comprising
   a manual device operable by hand to pressurize air and including a reservoir for storing air pressurized by said manual device, said reservoir being capable of storing a quantity of air sufficient to produce a series of positive air pressure pulses; and
   pressure transmitting means communicating with said reservoir and configured to communicate with the outer ear canal to deliver air from said reservoir as a series of positive air pressure pulses to the middle ear via the vent to displace the partition to influence fluid distribution in the inner ear, said pressure transmitting means being capable of delivering the series of positive air pressure pulses from said quantity of air stored in said reservoir without additional air being pressurized by said manual device.

2. The apparatus recited in claim 1 wherein said manual device includes a chamber having resilient walls and squeezable by hand to pressurize air therein and said reservoir receives air from said chamber.

3. The apparatus recited in claim 1 wherein said pressure transmitting means includes a plug for engaging the outer ear canal and an aperture in the plug through which the series of positive air pressure pulses is delivered.

4. Apparatus for treating a human ear having an outer ear canal separated from a middle ear by a tympanic membrane with a vent therethrough and an inner ear separated from the middle ear by a partition to treat the symptoms of Meniere's disease comprising
   a manual device,
   a chamber having resilient walls and squeezable by hand to pressurize air therein, and;
   pressure transmitting means communicating with said manual device and configured to communicate with the outer ear canal to deliver air pressure to the middle ear via the vent to displace the partition to influence fluid distribution in the inner ear, said pressure transmitting means including a reservoir communicating with said chamber for holding air pressure therein greater than ambient air pressure for delivery to the middle ear via the outer ear canal and the vent.

5. The apparatus recited in claim 4 wherein said pressure transmitting means includes means for delivering air pressure pulses to the middle ear via the outer ear canal and the vent.

6. The apparatus recited in claim 4 wherein said pressure transmitting means includes a passage communicating with said reservoir for delivering the air pressure from said reservoir as a static air pressure greater than ambient air pressure to the middle ear via the outer ear canal and the vent.

7. Apparatus for treating a human ear having an outer ear canal separated from a middle ear by a tympanic membrane with a vent therethrough and an inner ear separated from the middle ear by a partition to treat the symptoms of Meniere's disease comprising
   a manual device operable by hand to pressurize air; and
   pressure transmitting means communicating with said manual device and configured to communicate with the outer ear canal to deliver air pressure to the middle ear via the vent to displace the partition to influence fluid distribution in the inner ear, said pressure transmitting means including a passage delivering a static air pressure greater than ambient air pressure to the middle ear via the outer ear canal and the vent and means for generating air pressure pulses superimposed on said static air pressure to be delivered to the middle ear via the outer ear canal and the vent.

8. Apparatus for treating a human ear having an outer ear canal separated from a middle ear by a tympanic membrane with a vent therethrough and an inner ear separated from the middle ear by a partition to treat the symptoms of Meniere's disease comprising
   a hand-operated, manual air pressurizing device including a chamber, a first check valve in a first port communicating with said chamber allowing air to enter said chamber and preventing air from exiting from said chamber and a second check valve in a second port communicating with said chamber allowing air to exit said chamber and preventing air from entering said chamber; and a pressure transmitting arrangement communicating with said second port of said hand-operated manual air pressurizing device receiving pressurized air from said chamber via said second check valve and configured to communicate with the outer ear canal, said pressure transmitting arrangement including a flow regulator downstream of said second check valve and operable independently of said hand-operated manual air pressurizing device to deliver the pressurized air in pulses to the middle ear via the vent to displace the partition to influence fluid in the inner ear.

9. Apparatus for treating a human ear having an outer ear canal separated from a middle ear by a tympanic membrane with a vent therethrough and an inner ear separated from the middle ear by a partition to treat the symptoms of Meniere's disease comprising a hand-operated, manual air pressurizing device including a chamber, a first check valve in a first port communicating with said chamber allowing air to enter said chamber and preventing air from exiting from said chamber and a second check valve in a second port communicating with said chamber allowing air to exit said chamber and preventing air from entering said chamber; and a pressure transmitting arrangement communicating with said second port of said hand-operated manual air pressurizing device receiving pressurized air from said chamber and configured to communicate with the outer ear canal to deliver the air pressure to the middle ear via the vent to displace the partition to influence fluid in the inner ear, said pressure transmitting arrangement including a reservoir to establish a static air pressure greater than ambient air pressure for delivery to the middle ear via the outer ear canal and the vent.

10. The apparatus recited in claim 9 wherein said pressure transmitting arrangement includes a pressure regulator forming pressurized air pulses superimposed on said static air pressure for delivery to the middle ear via the outer ear canal and the vent.

11. The apparatus recited in claim 10 wherein said pressure transmitting arrangement includes a check valve disposed between said reservoir and said pressure regulator allowing air to enter said pressure regulator from said reservoir and preventing air from said pressure regulator from entering said reservoir.

12. The apparatus recited in claim 11 wherein said pressure regulator includes a pivotally mounted valve member forming said pressurized air pulses.

13. The apparatus recited in claim 12 wherein said manual air pressurizing device has resilient walls squeezable by hand.

14. A method for treating a human ear having a middle ear and an inner ear separated by a partition to treat the symptoms of Meniere's disease comprising the steps of manually pressurizing air, and thereafter delivering the manually pressurized air to the middle ear as a series of positive air pressure pulses to displace the partition to influence fluid distribution in the inner ear.

15. The method recited in claim 14 wherein said manually pressurizing step includes manually squeezing a resilient chamber.

16. A method for treating a human ear having a middle ear and an inner ear separated by a partition to treat the symptoms of Meniere's disease comprising the steps of manually pressurizing air; and delivering the manually pressurized air to the middle ear in pulses to displace the partition to influence fluid distribution in the inner ear, said delivering step including establishing a static air pressure in the middle ear greater than ambient air pressure and superimposing the pressurized air pulses on the static air pressure.

\* \* \* \* \*